Figure 2:
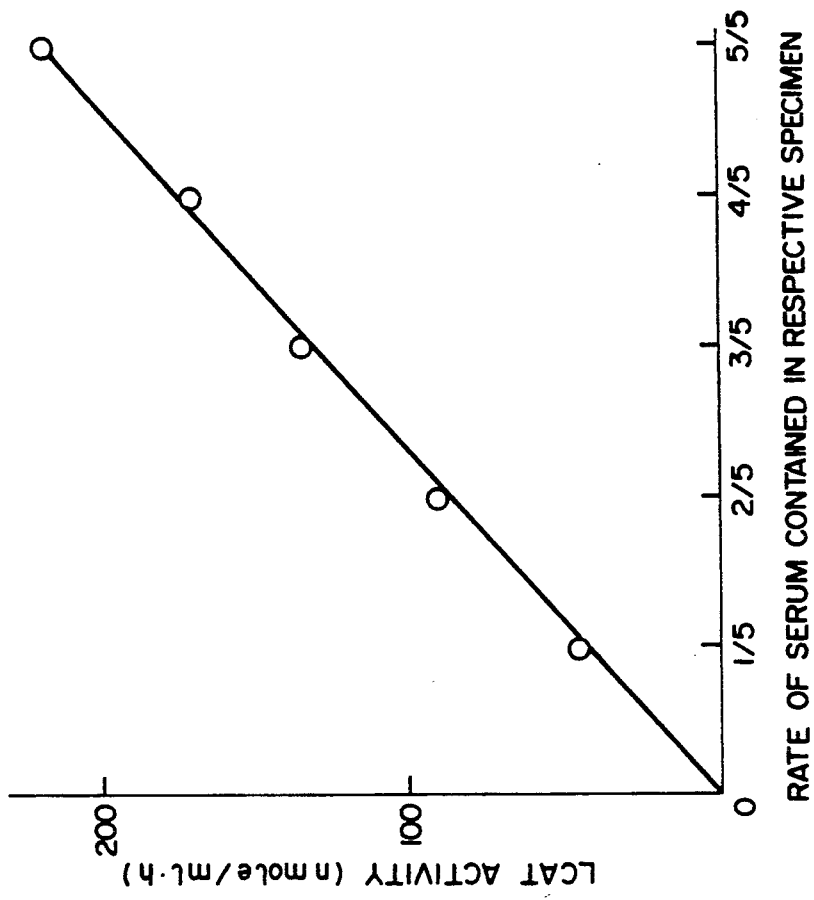

United States Patent [19]

Ueda et al.

[11] Patent Number: 5,122,454
[45] Date of Patent: Jun. 16, 1992

[54] ASSAY METHOD FOR LECITHIN-CHOLESTEROL ACYLTRANSFERASE

[75] Inventors: Shigerr Ueda; Hideo Misaki; Shigeyuki Imamura, all of Shizuoka, Japan

[73] Assignee: Toyo Yozo Company, Ltd., Shizuoka, Japan

[21] Appl. No.: 549,538

[22] Filed: Jul. 9, 1990

Related U.S. Application Data

[63] Continuation of Ser. No. 151,425, Feb. 2, 1988, abandoned.

[30] Foreign Application Priority Data

Mar. 20, 1987 [JP] Japan .................................. 62-67003

[51] Int. Cl.$^5$ .......................... C12Q 1/48; C12Q 1/00; C12Q 1/60; C12Q 1/44
[52] U.S. Cl. .......................................... 435/15; 435/4; 435/11; 435/19; 435/20; 435/26; 435/28; 435/810
[58] Field of Search ............... 435/11, 4, 15, 19, 20, 435/26, 28, 810

[56] References Cited

U.S. PATENT DOCUMENTS 4,370,318  1/1983  Umezawa et al. .................... 514/19
4,693,971  9/1987  Misaki ................................... 435/17

FOREIGN PATENT DOCUMENTS 2540237  1/1984  France .
262600  12/1985  Japan .
293396  12/1986  Japan .

OTHER PUBLICATIONS

Biological Abstracts, vol. 64, No. 6, Nov. 15, 1977, p. 34415 Abstract No. 34407, Soler-Argilaga, C. et al. "Effect of Triton . . .".
Lowenstein, J. M. *Methods in Enzymology*, vol. 71, part C pp. 753–767.
Shigeru Ueda, Hideo Misaki and Shigeyuki Imamura Japan Clinical Chemistry Abstract No. 232, vol. 32(6):1096 (1986).
Japan Clinical Chemistry, pp. 36 & 44 (1986).
Shigeru Ueda and Hideo Misaki, Japan Society of Clinical Chemistry 24:85 (1984).

*Primary Examiner*—David M. Naff
*Assistant Examiner*—L. Blaine Lankford
*Attorney, Agent, or Firm*—Darby & Darby

[57] ABSTRACT

An assay with high sensitivity for activity of lecithin-cholesterol acyltransferase in blood for functional analysis of liver, by bringing the blood into contact with lecithin and free cholesterol until lysolecithin and cholesterol ester are produced, allowing the lysolecithin produced to react with lysophospholipase and glycerophosphocholine phosphodiesterase and assaying glycerol-3-phosphate produced simultaneously or successively in the reaction by means of an enzymatic cycling reaction in which glycerol-3-phosphate, dihydroxyacetone-3-phosphate, nicotinamide adenine dinucleotide (NAD), reduced NAD, $O_2$, $H_2O_2$, glycerophosphate oxidase and glycerophosphate dehydrogenase take part.

9 Claims, 1 Drawing Sheet

ASSAY METHOD FOR LECITHIN-CHOLESTEROL ACYLTRANSFERASE

This is a continuation of application Ser. No. 151,425, filed Feb. 2, 1988, now abandoned.

This invention relates to an enzymatic assay method for lecithin-cholesterol acyltransferase (hereinafter referred to as "LCAT") in a specimen, and a composition usable therefor.

BACKGROUND OF THE INVENTION

LCAT is an enzyme which acts on lecithin and free cholesterol as the substrates in blood to produce lysolecithin and cholesterol ester, said enzyme being biosynthesized in liver. Assay of LCAT is useful for liver function test and is also useful for pathologic study of lipoids metabolism disorder and diabetes mellitus, since activity of LCAT has a relation to disorder of liver cells. For example, LCAT is decreased in the cases of acute hepatitis, liver cirrhosis, closed jaundice and cancer of the liver, while increased in the cases of alcoholic liver disease and fatty liver.

Hitherto, assay of this enzyme has been carried out by determining change of an amount of free cholesterol consumed as substrate. Practically, it is conducted by warming blood serum (or blood plasma) for a definite period of time (e.g. 2 hours) at an optimal reaction temperature of 37° C and determining change of an amount (n mole) of free cholesterol before and after the warming. The activity is indicated as a changed amount of n mole per ml of blood serum per hour (h), i.e., n mole/(ml·h).

Reaction rate of enzymes is usually indicated by that in the initial stage of a reaction where an enough amount of substrate exists in a reaction solution and reaction curve is linear relative to time. However, in the case of LCAT, assay is very difficult because the reaction occured in high density lipoprotein, apoprotein A-1 in high density lipoprotein acts as an activating factor for the enzyme and furthermore lecithin and cholesterol are essentially insoluble in water. Assay methods are divided into two main classes namely, the common substrate method where an excessive amount of substrate having no LCAT activity is added to a small amount of blood serum (or blood plasma), and the self -substrate method where the blood serum (or blood plasma) is warmed directly and endogenous lipoprotein is used as a substrate. In the latter case, it is difficult to determine change of amount of free cholesterol by spectrophotometrical analysis unless the warming time is made long, since reactivity of LCAT itself is essentially very small and linearlity of parameters is lost within one hour after initiation of the reaction when serum (or plasma) itself is warmed at 37° C.

In order to dissolve difficulties mentioned above, there are many proposals. One approach is that lecithin comprising a surfactant is added to a specimen (Japanese Unexamined Patent Publication No. Sho 51-129293). This method is not satisfactory yet from a view point of clinical inspection, because the absence of free cholesterol, another substrate for LCAT, lowers the LCAT activity, and the surfactant added to solubilization of lecithin inhibits the LCAT activity.

Another approach is a treatment of a sample solution containing lecithin and free cholesterol as substrates treated by sonication in order to make it transparent and solubilized [Clinical Chemistry, Vol. 4, collected No. 3-4, 306-311, (1976)]. However, this approach is hardly applicable to clinical inspection, because the ultrasonic treatment only temporarily reduces turbidity of the solution but does not make it transparent and precipitation is produced after 2-3 hours.

The other approaches are those wherein incubation time of a specimen is reduced by keeping linearity of LCAT reaction or by increasing the activity thereof. For example, they include an assay of LCAT activity wherein polyanionic sugar derivatives are added to make cholesterol and lecithin transparent (Japanese Unexamined Patent Publication No. Sho 60-262600), and an assay of LCAT activity wherein a liposome comprising cholesterol and lecithin is added (referred to as "liposome method") [the 26th meeting of the Society of Clinical Chemistry held on Nov. 22, 1986, (Gist of the report, pp 100-101, 1986)]. However, these methods are not satisfactory yet, either, as enzyme, assay, since reaction time (incubation time) is longer than 40 minutes for the liposome method, and at least 1 hour for the other methods. Furthermore, these assays encounter difficulty in practical clinical inspection, since rapid assay is hardly effected. Even in the liposome method which requires the shortest period of time nowadays, it is very difficult to prepare homogeneous, stable liposome, and thus, it is difficult, indeed, to always supply liposome of the definite composition to the site of clinical diagnoses in general.

Recently, an assay for LCAT of exogenic lecithin and cholesterol esterase (Japanese Unexamined Patent Publication No. Sho 61-293396). This method involves also drawbacks in that it requires reaction time of longer than one hour to measure the increased amount of lysolecithin. As above mentioned, such a method is not desirable from a point of rapid measurement. Such a long reaction time owes to the limit of sensitivity of colorimetry.

SUMMARY OF THE INVENTION

The inventors have found an assay method for LCAT by which daily inspection is carried out rapidly and easily with high sensitivity.

The present invention is based on the fact that LCAT activity is assayed by bringing a specimen containing LCAT into contact with a substrate comprising lecithin and free cholesterol, until lysolecithin and cholesterol ester are produced, allowing lysophospholipase (EC, 3.1.1.5; hereinafter referred to as LYP) and glycerophosphocholine phosphodiesterase (EC, 3.1.4.2; hereinafter referred to as GPCP) to react with the lysolecithin produced above, and measuring an amount of glycerol-3-phosphate (hereinafter referred to as G3P) produced thereby simultaneously or successively by use of an enzymatic cycling method with high sensitivity. Furthermore, the present invention is based on the fact that LCAT assay is conducted rapidly, accurately and easily by using a composition containing LYP, GPCP, glycerophosphate oxidase (hereinafter referred to as GPO) and reduced nicotinamide adenin dinucleotide (hereinafter referred to as reduced AND).

According to the present invention, an assay method for LCAT in a specimen to be assayed with high sensitivity is provided, which comprises bringing the specimens into contact with a substrate comprising lecithin and cholesterol until lysolecithin and cholesterol ester are produced, allowing lysophospholipase and glycerophosphocholine phosphodiesterase to react with the resulting lysolecithin and measuring an amount of glycerol-3-phosphate produced simultaneously or successively thereby by use of an enzymatic cycling method and further a composition for conducting the said method for assaying LCAT is provided which comprises LYP, GPCP, GPO and reduced AND.

In an assay method for LCAT by using an enzyme reaction system as expressed by the formula (i) and measuring an amount of lysolecithin produced thereby or the rate of production thereof,

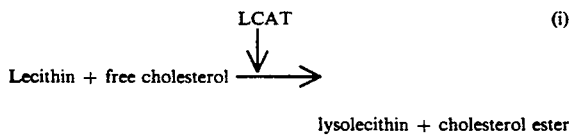

the conventional method required a very long time and was unable to afford an easy measurement, since either an amount of produced lysolecithin or the production rate thereof was very small. The present invention provides a method capable of conducting the LCAT assay rapidly and easily in practical clinical examination by combining an enzyme reaction of the formula (ii) and an enzymatic cycling system of the formula (iii) with the enzyme reaction system of the formula (i).

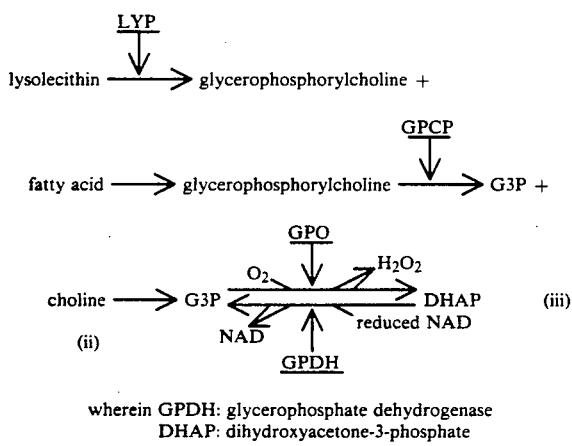

wherein GPDH: glycerophosphate dehydrogenase
DHAP: dihydroxyacetone-3-phosphate

In the present invention, the substrates necessary for performing the reaction system of the formula (i) are lecithin and free cholesterol. However, it is not always necessary to add lecithin and/or free cholesterol to carry out the invention when a specimen to be assayed is blood serum or blood plasma, since there are lecithin and free cholesterol therein.

An exogenous lecithin may be added to supplement the shortage of lecithin due to the LCAT reaction. Examples of the exogenous lecithin include dipalmitoyl phosphatidylcholine, dioleylphosphatidylcholine, dimyristoylphosphatidylcholine, distearoylphosphatidyl choline, dilauroylphosphatidylcholine, natural lecithin or various lecithins treated by sonication. Further, a substrate which does not inhibit the LCAT activity, such as, liposome consisting of lecithin and cholesterol may be added. Alternatively, a cholesterol ester hydrolase may be added advantageously in the LCAT reaction system, since free cholesterol consumed in the LCAT reaction is supplemented and the initial concentration of endogenous free cholesterol is increased thereby, or the LCAT enzymatic reaction is accelerated by allowing the cholesterol ester hydrolase to react with endogenous cholesterol ester or that produced by the LCAT reaction. This serves to improve assay sensitivity.

The cholesterol ester hydrolase are hydrolases which react with cholesterol ester to produce free cholesterol. Namely, such cholesterol hydrolase includes so-called cholesterol esterase (hereinafter referred to as CHE) as well as those called lipase and esterase having said enzymatic action. Examples of CHE include those derived from animal tissues such as pancreas, liver, brain adrenal gland, testis and ovary; and those derived from microorganisms such as *Pseudomonas fluorescens Schizophyllum comune* and *Chromobacterium viscosum*. Examples of lipase include those derived from animal tissues such as pancreas, liver and fat tissue, those derived from plant seeds, and those derived from microorganisms such as *Pseudomonas fluorescens* and *Geotricum candidum*. These cholesterol esterase may be used used in an amount of at least 1U, preferably 1–70U per test.

Lysolecithin produced by the LCAT enzyme reaction as indicated by the formula (i) is converted to G3P and choline by the two-step enzyme reactions as indicated by the formula (ii). In this enzyme reaction, lysophospholipase(LYP) is usually used in an amount of 0.3–10U/test, preferably, 0.5–3 U/test, and glycerophosphocholine diesterase (GPCP) in an amount of 0.3–10 U/test, preferably 0.5–3 U/test.

In the present invention, an assaying method for glycerol-3-phosphate (G3P) using the enzymatic cycling method as indicated by the formula (iii) (USP 93971) is applied to G3P formed by the enzymatic reaction (ii). This application of the formula (iii) facilitates rapidly measurement of LCAT activity with ease and with high sensitivity in practical clinical examination in spite of the complicated enzymatic reactions including various enzyme reaction systems.

The initial components participating in the enzymatic cycling reaction of the formula (iii) are GPO, GPDH, $O_2$ and reduced AND. In this enzymatic cycling reaction (iii), GPO consumes 1 molecule each of G3P and $O_2$ to produce 1 molecule each of $H_2O_2$ and DHAP, and further, using this DHAP as a substrate, GPDH consumes 1 molecule each of DHAP and reduced AND to produce 1 molecule each of G3P and AND, thus forming a G3P-DHAP cycle reaction system.

In the formula (iii), GPO, GPDH, $O_2$ and reduced AND are essential to form this enzymatic cycling reaction. However, in practice, $O_2$ dissolved in the reaction system is enough, so far as $O_2$ is concerned, and GPO, GPDH and reduced AND are used in excess as reactants for the measurement. Amounts of GPO and GPDH to be used in the reaction are not limited specifically, but may be determined based on the sum of amounts of G3P derived from endogenous lysolecithin contained in the specimen and G3P estimated to be produced on the basis of the LCAT activity, taking into consideration of balance between the amounts of GPO and GPDH and that of G3P GPO is usually used in an amount of 5–20 U, preferably 8–15 U, and GPDH 0.3–1.8 U, preferably 0.5–1.5 U, per test of specimen, but these enzymes may be used in amounts more than that above mentioned. Reduced AND may be used in an amount more than Km value of GPDH for reduced AND. Reduced AND is usually used in an amount greatly larger than that of G3P, for example, at least 50 times, preferably 100–1000 times, as much as the latter. Much more reduced AND may be used.

Furthermore, sensitivity for LCAT activity is made higher by a modification, i.e., doubly sensitive, by allowing the reduced AND to react with $H_2O_2$, to form AND. Namely, this modification method is illustrated by the formula (iv) as below:

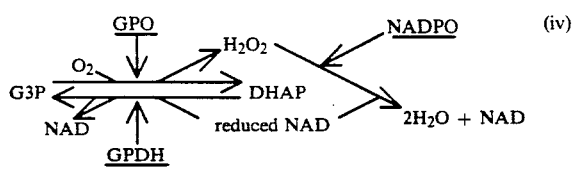

wherein NAD+peroxidase (EC, 1.11.1.1; hereinafter referred to as NADPO) [J. Biol. Chem., 22, 5, 557 (1957)], is used in combination, which is an enzyme capable of catalyzing a reaction to consume 1 molecule of $H_2O_2$ and 1 molecule of reduced AND in the enzyme cycling reaction iii) until 2 molecules of water ($H_2O$) and 1 molecule of AND are produced. In the enzyme reaction (iv), 2 molecules of reduced AND are consumed per cycle, since $H_2O_2$ formed in the enzyme cycling reaction (iii) is further consumed together with reduced AND to form AND. That is, LCAT assay is conducted with higher sensitivity than the reaction (iii) alone, since an amount of reduced AND changed becomes twice as much as that in the reaction (iii) alone.

Any medium may be employed in various enzyme reactions and enzymatic cycling reactions as above described, as long as it has a pH range in which activities of various enzymes are stable. Usually, for the present LCAT assay, the medium has a pH of 7.0–8.5, preferably 7.3–8.2. Examples of the buffer solution for the medium are phosphate buffer solution, tris-hydrochloric acid buffer solution, imidazole-hydrochloric acid buffer solution, dimethyl glutarate-sodium hydroxide buffer solution, PIPES buffer solution, HEPES buffer solution, etc., in which pH is controlled in the above mentioned range. Metal salts such as calcium salts and magnesium salts, an activating agent for LYP and GPCP, may be added to the medium. For example, calcium chloride, one of calcium salts, may be added in a concentration of 1–10 mM, preferably 2–6 mM. Incubation is usually carried out at a temperature of about 37° C.

When the enzyme reactions (i) and (ii) and the enzymatic cycling reaction (iii) or (iv) are performed simultaneously, the reaction is conducted for at least 5 minutes, preferably 5–10 minutes, to ensure rapidness of measurement. When the enzyme reactions (i) and (ii) and the enzymatic cycling reaction (iii) or (iv) are successively performed, the enzyme reaction (i) is conducted for at least 10 minutes and the enzyme reaction (ii) and the enzymatic cycling reaction (iii) or (iv) for at least 2 minutes, respectively. Furthermore, when the enzyme reaction (i) is performed before the enzyme reaction (ii) and the enzymatic cycling reaction (iii) or (iv) are simultaneously performed, the enzyme reaction (i) is conducted for at least 10 minutes, and the enzyme reaction (ii) and enzymatic cycling reaction (iii) or (iv) for at least 2 minutes.

After the reactions above described are over, an amount of change or a rate of change caused by the reaction is quantitatively measured. Detectable parameters for change in amount are those which are consumed or produced 1 mole ratio or 2 mole ratio in one cycle of the enzymatic cycling reaction (iii) or (iv) wherein 1 mole ratio of G3P or DHAP is formed or consumed. They are $O_2$ consumed, reduced AND consumed, or $H_2O_2$ produced.

$O_2$ consumed is measured as an amount of electrochemical change using an oxygen electrode. Reduced AND consumed is calculated from difference between an amount of reduced AND used before the reaction and that remaining after the reaction. Reduced AND remaining after the reaction or used before the reaction are measured by various known methods. One of them is absorptiometry not on the basis of specific absorbancy of coexisting AND but that of reduced AND. Specific absorption maximum for measurement of reduced AND lies in the vicinity of 320–360 nm, preferably 340 nm. Remaining amount of reduced AND is measured using this wave length. Another method for reduced AND is colorimetry by use of an electron transport chromogen having an electron acceptor from reduced AND. Examples of electron transport chromogen are tetrazolium salts and 2,6-dichlorophenolindophenol, preferably a combination of water-soluble tetrazolium salt and diaphorase or phenazine methosulfate. The electron transport chromogen colors with a hydrogen atom of reduced AND. Formazan color produced is chlorimetrically observed at the maximum absorption such as 500–550 nm. Another method for reduced AND is fluorometry in which diaphorase is applied to in the presence of a fluorescent agent such as resazulin. Especially when the enzymatic reaction (iv) is performed, measurement of reduced AND is preferred as a doubly sensitive assay for LCAT, since an amount of change of reduced AND converted is twice as much as that of the enzymatic cycling reaction (iii) alone. Measurement of $H_2O_2$, which is a generated component, is based on electrochemical change by use of a hydrogen peroxide electrode, or on a product formed with an indicator composition which reacts with $H_2O_2$. Examples of indicators are a color indicator which causes change of color tone in the visible range, a fluorescent reagent which fluoresces by excitation light or a luminescent reagent whose change is detectable by spectrophotometrical means.

Parameters of detectable changing rates caused by the enzymatic cycling reaction (iii) or (iv) are decreasing rate of $O_2$ consumed by the reaction, decreasing rate of reduced AND consumed and increasing rate of $H_2O_2$ generated by the reaction. The changing rate is in proportion to an amount of a substrate when the enzymatic cycling reaction reaches stationary state in a short period. Assay of LCAT in a specimen is made by measuring change in the rate before and after the LCAT reaction, for example, decreasing rate of reduced AND before and after the reaction at 340 nm by use of a spectrophotomer, decreasing rate of $O_2$ by use of an oxygen electrode,or increasing rate of $H_2O_2$ by use of a hydrogen peroxide electrode.

Practical assay of LCAT is conducted as follows. For example, a sample of blood serum or plasma is divided and poured into two test tubes. Into one of the tubes, is added an LCAT inhibitor, for example, cholic acid or at least 1% of Triton X-100 (trade name: manufactured by Sigma Co.), a given amount of cholesterol ester hydrolase is added thereto, and the tube is cooled with ice (A). Into another test tube, is added a given amount of cholesterol ester hydrolase, the tube is incubated at 37° C. for a given time, usually longer than 10 minutes, preferably 10–20 minutes, and an LCAT inhibitor is added to stop the enzyme reaction based on the LCAT activity (B). Then, given amounts of the sample solutions are taken from the tubes, respectively, to which are added an LCAT assay agent, respectively, containing reduced AND, LYP, GPCP, GPO and GPDH. Decreasing rate of reduced AND is spectrophotometrically measured at 37° C. at 340 nm or increasing rate of H$_2$O$_2$ is measured by use of a hydrogen peroxide electrode. In the same manner as above, after a given amount of G3P solution of known concentration (standard solution)is added to the LCAT assay agent, decreasing rate of reduced AND or increasing rate of H$_2$O$_2$ is measured (Rc). From these values,LCAT activity is calculated according to the following equation:

$$U = \frac{R_B - R_A}{R_C} \times S \times \frac{1}{T} \times f$$

wherein

U : LCAT activity (n mole/(ml·h)),

R$_A$ : decreasing rate of reduced AND (or increasing rate of H$_2$O$_2$) in specimen in the test tube A, R$_B$ : decreasing rate of reduced AND (or increasing rate of H$_2$O$_2$) in specimen in the test tube B, R$_C$ decreasing rate of reduced AND (or increasing rate of H$_2$O$_2$) in the standard solution, S concentration of the standard solution (n mole/ml), T : incubation time before addition of an LCAT activity inhibitor the test tube B (h), and f : correction value based on the difference in dilution degree of the specimen solution and the standard solution.

Specimen required for the LCAT assay in the present invention is usually, 2–30μl, preferably 4–16 μl. Sensitivity of assay is to be determined according to balance between an amount of endogenous lysolecithin (as a practical example, R$_A$/R$_C$×S×f) and activity of LCAT [(R$_B$−R$_A$)/R$_C$×S×f]. Normal range of lysolecithin has not been determined clinically. In the invention, when about 5 μl of specimen is used, enough sensitivity is obtained at incubation time (T) of 15 minutes. Sensitivity is improved when the rate of cycling of the enzymatic cycling reaction (iii) is controlled by adjustment of the quantity of GPO and GPDH.

When assay of LCAT is conducted according to the above described method, it is considered that an error is caused by the possible presence of active phospholipase A$_2$ (EC, 3.1.1.4; hereinafter referred to as PLPA$_2$) which is an enzyme producing lysolecithin and free fatty acid by a reaction with lecithin and water in the specimen. However, little effect has been observed in the assay of LCAT with reference to more than ten specimens. In treatment of the test solution in the test tube (A), the LCAT activity may be assayed regardless of the active amount of PLPA$_2$ possibly existing in the specimen to be assayed, by adding a given amount of an LCAT inhibitor, adding properly a given amount of cholesterol ester hydrolase, incubating at 37° C. for a given period of time and then cooling with ice. Therefore, the LCAT assay method may be properly replaced by this method. When assay of LCAT is conducted by performing the enzymatic reaction (i), (ii) and (iii) simultaneously, a component is added which inhibits only the activity of PLPA$_2$ but not that of other enzymes.

Thus, the invention provides a novel LCAT assay method, and also provides a composition for the LCAT assay which contains LYP, GPCP, GPO, GPDH and reducing AND, essential for the novel assay method.

The invention enables to carry out a simple and rapid assay of LCAT in the clinical diagnoses.

To the composition of the invention, may be added various solvents mentioned hereinbefore relating to the assay method. The enzymes LVP, GPCP, GPO and GPDH and substrate, reduced AND, may be provided all together or separately before or after freeze-drying is made by a known method so that they are usable by dissolving or dispersing in a proper prescribed amount of a solvent for the measurement.

The invention will be described hereinafter with reference to examples, but it is to be understood that the invention is not limited thereto.

Figure 1:
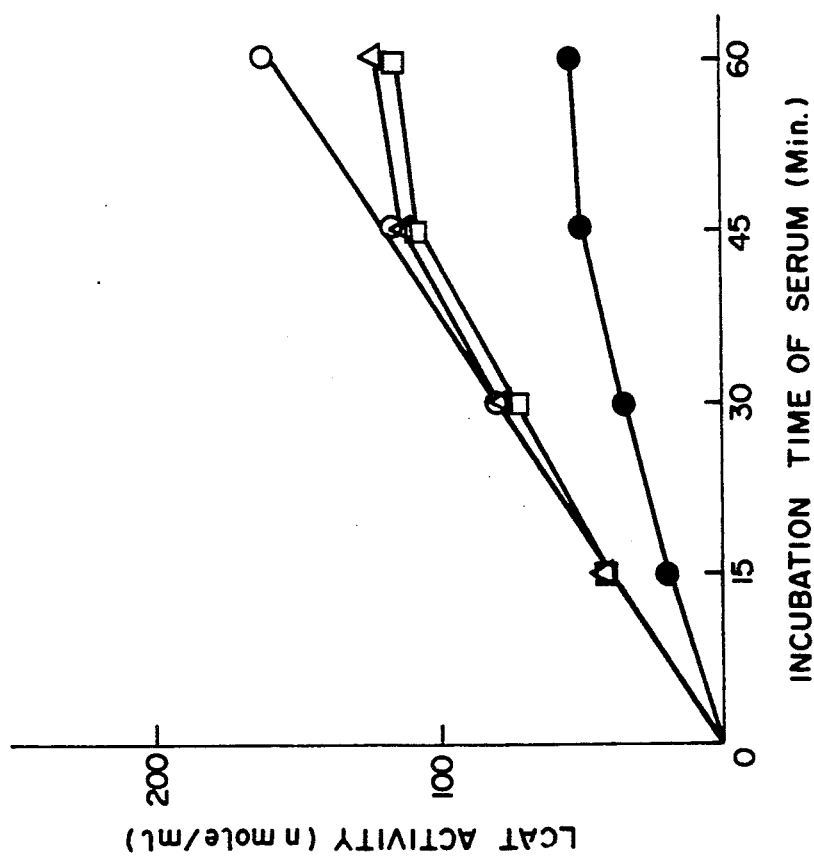

Referring to the accompanying drawings, FIG. 1 shows curves of change of LCAT activities vs. incubation time of blood serum depending on cholesterol esterase added and FIG. 2 shows a calibration curve.

EXAMPLE 1

(1) Preparation of the reagent for LCAT assay

Lysophospholipase; [(LYP); Toyo Jozo Co., Ltd., originated from Vibrio genus], 10 unit, glycerophosphocholine phosphodiesterase [(GPCP); Toyo Jozo Co., Ltd.; originated from a microorganism, Toyo Jozo Belletin No. T-33, 10 unit, glycerophosphate oxidase [(GPO): Toyo Jozo Co., Ltd.; originated from Aerococcus], 160 unit, and glycerophosphate dehydrogenase [(GPDH); Boehringer.Mannheim AG; originated from rabbit muscles, 68 unit, were dissolved in a buffer solution (pH 8.0) of 40 mM HEPES containing 5 mM of calcium chloride and 0.25 mM of reduced AND (NADH), to obtain 20 ml of a solution.

(2) LCAT assay

Four specimens of serum were used. Each 0.1 ml of the specimen was poured, respectively,into two test tubes, to one of which was added cholesterol esterase [(CHE); Toyo Jozo Co. Ltd., originated from Pseudomonas], 1.4 unit, or lipase [(LP) ; Toyo Jozo Co. Ltd., originated from Chromobacterium], 5 unit. Two tubes were cooled with ice. Each 5 μl of the specimen was added to 1 ml of the reagent for LCAT assay, and, after incubation at 37° C. for 5–6 minutes, change of absorbance was measured at 340 nm. The two tubes were incubated at 37° C. for 15 minutes and added thereto 5 μl of Triton X-100, to stop the LCAT reaction. Then, 5 μl of each of the specimens was added to 1 ml of the agent for LCAT assay, and the mixture was incubated at 37° C. for 5–6 minutes, and measured the change of absorbance at 340 nm. Further, with reference to 5 μl of 200 μM glycerol-3-phosphate, the measurement was conducted in the same manner as above. The values of LCAT assay were calculated by using the above described calculation formula. With every specimen, addition of cholesterol ester hydrolase exhibited activity of 2–3.5 times as much as that without the enzyme. The results are shown in Table 1. In the invention, although the addition of cholesterol ester hydrolase is exemplified as a proper example, the case wherein no enzyme was added also showed a satisfactory value.

TABLE 1

| | Value of LCAT assay (n mole/(ml · h)) | | |
|---|---|---|---|
| | no addition | CHE added | LP added |
| Serum 1 | 58 | 202 | — |
| Serum 2 | 112 | 220 | — |
| Serum 3 | 84 | 258 | — |

TABLE 1-continued

| | Value of LCAT assay (n mole/(ml · h)) | | |
|---|---|---|---|
| | no addition | CHE added | LP added |
| Serum 4 | 34 | 102 | 102 |

EXAMPLE 2

(1) Preparation of the reagent for LCAT assay

Lysophospholipase (same as above), 10 unit, glycerophosphocholine phosphodiesterase (same as above), 10 unit, glycerophosphate oxidase (same as above), 160 unit, and glycerophosphate dehydrogenase (same as above), 68 unit, were dissolved in a buffer solution (pH 8.0) of 40 mM HEPES containing 5 mM of calcium chloride and 0.25 mM of reduced AND (NADH), to obtain 20 ml of a solution.

(2) LCAT assay

With reference to one specimen, each 0.1 ml thereof was poured into three tubes. To the respective tubes were added cholesterol esterase in an amount of, respectively, 1.4 unit, 14 unit and 70 unit per ml. The respective tubes were incubated at 37° C. for a proper time and then thereto were added 5 μl of 10% Triton X-100 to stop the LCAT reaction. To each 5 μl of the reacted mixture, was added 1 ml of the reagent for LCAT assay, and, after incubating at 37° C. for 5-6 minutes, the change of absorbance at 340 nm was measured. Further, the same measurement was carried out with reference to a sample of 5 μl of 200 uM glycerol-3-phosphate. The values of LCAT assay vs. time were calculated by use of the above calculation formula. The results are shown in FIG. 1 in which incubation time of serum is taken as abscissa and LCAT activity as ordinate, —O—, —□— and —△— are for 1.4 U/ml, 14 U/ml and 70 U/ml of cholesterol esterase, respectively, and —●—: for serum only. The curves show that the longer reaction time is, the lower the LCAT activity is depending on cholesterol esterase. This may be due to decomposition of high density lipoprotein whose structure is indispensable for the LCAT reaction. However, substantially no influence is observed in the measuring time shorter than 20 minutes, which time is preferable for the LCAT assay in the present invention. In view of the results from Example 1, it is apparent that addition of cholesterol ester hydrolase gives remarkable influence to the system of LCAT assay in which measurement is possible within a short time with high accuracy as in the assay method of the present invention.

EXAMPLE 3

(1) Preparation of the reagent for LCAT assay

Lysophospholipase (same as above), 5 unit, glycerophosphocholine phosphodiesterase (same as above), 5 unit, glycerophosphate oxidase (same as above), 150 unit and glycerophosphate dehydrogenase (same as above), 34 unit, were dissolved in a buffer solution (pH 8.0) of 40 mM HEPES containing 5mM of calcium chloride, 0.25 mM of reduced AND (NADH) and 0.1% Triton X-100 to form 10 ml of a solution.

(2) Assay of LCAT activity

Four specimens were tested. Each 0.1 ml of the specimen was poured into two test tubes. To one of which was added 5 μl of 10% Triton X-100 and 0.2 unit of cholesterol esterase (same as above), and then the mixture was cooled with ice. To the other tube was added 0.2 unit of cholesterol esterase (same as above). The tubes were incubated at 37° C. for 15 minutes, then 5 μl of 10% Triton X-100 was added to stop the LCAT reaction. Then, to each 5 μl of the mixture was added 1 ml of the reagent for LCAT assay, and after incubation at 37° C. for 5-6 minutes, the change of absorbance was measured at ° 340 nm. Similar test was applied to a specimen(5 μl) of 200 μM glycerol-3-phosphate. Then, LCAT activities were calculated on the basis of the above calculation formula. The results are shown in Table 2.

TABLE 2

| | Value of LCAT assay (n mole/(ml · h)) |
|---|---|
| Serum 1 | 204 |
| Serum 2 | 220 |
| Serum 3 | 258 |
| Serum 4 | 102 |

Furthermore, specimens were prepared by diluting the blood serum 2 to 4/5, 3/5, 2/5 and 1/5 ratios, respectively. Each of the diluted specimen was measured for the LCAT activity, and a calibration curve was prepared. It shows very good linearity as exhibited in FIG. 2 (the abscissa being the rates of serum contained in each specimen, and the ordinate being the LCAT activity).

EXAMPLE 4

(1) Preparation of the reagent for LCAT assay

Reagent 1 : Lysophospholipase (same as above), 5 unit, glycerophosphocholine phosphodiesterase (same as above), 5 unit, and giycerophosphate dehydrogenase (same as above), 8.5 unit, were added to a buffer solution (pH 8.0) of 50 mM HEPES containing 5mM of calcium chloride, 0.25 mM of reduced AND (NADH) and 0.1% of Triton X-100, to obtain 5 ml of a solution.

Reagent 2 : Glycerophosphate oxidase (same as above), 160 unit, was added to a buffer solution (pH 8.0) of 50 mM HEPES, to obtain 1 ml of a solution.

Reagent 3 : 1.5% sodium dodecylsulfate solution.

(2) LCAT assay

Two specimens of serum were used. Each 0.05 ml of the specimen was added to respectively two test tubes. To one of the tubes, 5 μl of 10% Triton X-100, and then 0.5 unit of cholesterol esterase (same as above) were added, and the mixture was cooled with ice. To the other tube, was added 0.5 unit of cholesterol esterase (same as above). The tube were incubated at 37° C. for 15 minutes, and then 5 μl of 10% Triton X-100 was added thereto to stop the LCAT reaction. Each 5 μl of the sample taken from the respective tubes was added to 0.5 ml of Reagent 1 previously warmed,and, after the mixture was warmed at 37° C. for 5 minutes, 0.05 ml of Reagent 2 was added. After further warming was made at 37° C. for 5 minutes, 0.5 ml of Reagent 3 was added t the mixture, to stop the enzymatic cycling reactio. Each 0.01 ml of the sample was taken from the reaction mixture. After Reagent 2 was added thereto, the amount increased of hydrogen peroxide was measured during 5 minutes continuously by use of hydrogen peroxide electrodes. The similar test was conducted to a sample of 5 μl of a solution of glyceral-3-phosphate (200 μM). The values of LCAT activities of th specimens were calculated by use of the above calculation formula. The results are shown in Table 3.

TABLE 3

| | Value of LCAT assay (n mole/(ml · h)) |
|---|---|
| Serum 5 | 108 |
| Serum 6 | 232 |

REFERENCE EXAMPLE 1

(1) Preparation of the ragent for measuring lysolecithin

Lysophospholipase (same as above), 10 unit, glycerophosphocholine phosphodiesterase (same as above), 10 unit, glycerophosphate oxidase (same as above), 160 unit, and glycerophosphate dehydrogenase (same as above), 68 unit, were dissolved in a buffer solution (pH 8.0) of 40 mM HEPES containing 5 mM of calcium chloride and 0.25 mM of reduced AND (NADH), to obtain 20 ml of a solution.

(2) Lysolecithin assay

Three serum specimens were used. To a test tube was added each 0.1 ml of serum, to which was added 5 μl of 10% Triton X-100, to stop the LCAT reaction. Then, 1.4 unit of cholesterol esterase (same as above) was added thereto, and the tube was incubated at 37° C. With lapse of the reaction time, each 5 μl of the sample was taken from the respective tubes, and was added to 1 ml of the reagent for lysolecithin assay. The sample was incubated at 37° C. After 5-6 minutes, the change of absorbance was measured at 340 nm to determine an amount of lysolecithin. The results are shown in Table 4.

TABLE 4

| Serum incubation time | Amount of lysolecithin (μ mole/l) | | |
|---|---|---|---|
| | Serum 7 | Serum 8 | Serum 9 |
| 0 min | 235 | 212 | 180 |
| 15 min | 234 | 214 | 181 |
| 30 min | 237 | 212 | 178 |
| 45 min | 230 | 213 | 180 |

As apparent from the above Reference Example, no increase in lysolecithin originated from active phospholipase $A_2$ was observed.

As described above, according to the invention, assay of lecithin-cholesterol acyltransferase is conducted sensitively, rapidly and easily, so that the method is applicable in practical clinical examinations

We claim:

1. A method for assaying the activity of lecithin-cholesterol transferase (LCAT) in a specimen selected from the group consisting of blood serum and blood plasma by (a) reaction of lecithin and free cholesterol substrates, which are present endogenously in or added to said specimen, under the catalytic action of endogenous LCAT to produce lysolecithin and cholesterol ester, and (b) subsequently contacting the lysolecithin then present in said specimen with lysophospholipase and glycerophosphocholine phosphodiesterase to produce glycerol-3-phosphate (G3F), the improvement comprising:

(a') between step (a) and step (b) stopping said reacting lecithin and free cholesterol by inhibiting LCAT;

(b') simultaneously with or following performance of said step (b), assaying the G3F produced by step (b), by i) reacting the G3P in said specimen with glycerophosphate oxidase (GPO) and glycerophosphate dehydrogenase (GPDH), said reacting being in accordance with the following cycling reaction:

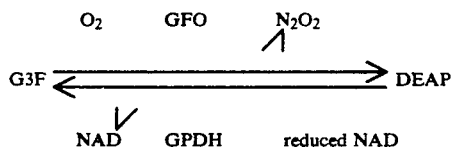

wherein AND is nicotinamide adenine dinucleotide; DHAF is dihydroxyacetone-3-phosphate; and $O_2$ is oxygen;

said cycling reaction resulting in detactable changes in amount or rate of consumption or production of the components consumed or products produced in said cycling reaction; and ii) measuring at least one of said detactable changes, thereby arriving at a value which correlates with the amount of lycolecithin produced in said step (a) and, hence, also correlates with the amount of endogenous LCAT in said specimen.

2. An assay method according to claim 1, in which, in the cycling reaction, NAD +peroxidase is added which catalyses a reaction to produce 2 molecules of $H_2O$ and 1 molecule of AND from 1 molecule of $H_2O_2$ and 1 molecule of reduced AND thereby reducing the rate of production or increasing the rate of consumption of reduced NAD.

3. An assay method according to claim 1, wherein said at least one of said detectable changes is the amount or rate of $O_2$ consumption.

4. An assay method according to claim 1, wherein said at least one detectable changes is the amount or rate of $H_2O_2$ production.

5. An assay method according to claim 1, wherein said at least one change is the amount or rate of consumption of reduced NAD.

6. An assay method according to claim 1, wherein cholesterol esterase is added to the specimen, said esterase being able to hydrolyze cholesterol estes produced in the reaction catalyzed by LCAT in said step (a).

7. The method of claim 1 wherein step (a) is conducted at about 37° C.

8. The method of claim 1, wherein the first reacting step (a) is conducted in a medium having a pH of 7.0-8.5.

9. The method of claim 8, wherein said medium has a pH of 7.3-8.2.

* * * * *